United States Patent [19]
Carol

[11] Patent Number: 5,368,543
[45] Date of Patent: Nov. 29, 1994

[54] TISSUE COMPENSATION APPARATUS

[75] Inventor: Mark P. Carol, Milford, N.Y.

[73] Assignee: Nomos Corporation, Sewickley, Pa.

[21] Appl. No.: 77,660

[22] Filed: Jun. 17, 1993

Related U.S. Application Data

[62] Division of Ser. No. 791,041, Nov. 12, 1991, Pat. No. 5,242,372.

[51] Int. Cl.5 .................................................. A61N 5/00
[52] U.S. Cl. ........................................................ 600/1
[58] Field of Search ........................................ 600/1-8; 128/897-898; 250/505.1; 33/511-512; 378/64, 65, 159

[56] References Cited

U.S. PATENT DOCUMENTS

| | | | |
|---|---|---|---|
| 2,216,326 | 10/1940 | Smith | 378/159 |
| 4,868,843 | 9/1989 | Nunan | 378/65 |
| 5,019,713 | 5/1991 | Schmidt | 378/65 |

Primary Examiner—Kyle L. Howell
Assistant Examiner—J. P. Lacyk
Attorney, Agent, or Firm—Ben D. Tobor

[57] ABSTRACT

A tissue compensation system and method for making a tissue compensator utilizes a plurality of elongate rods, one end of which contact the treatment surface on the patient, and the other end of which contact and deform a flexible membrane containing a quantity of a material substantially equivalent to tissue of the patient.

12 Claims, 7 Drawing Sheets

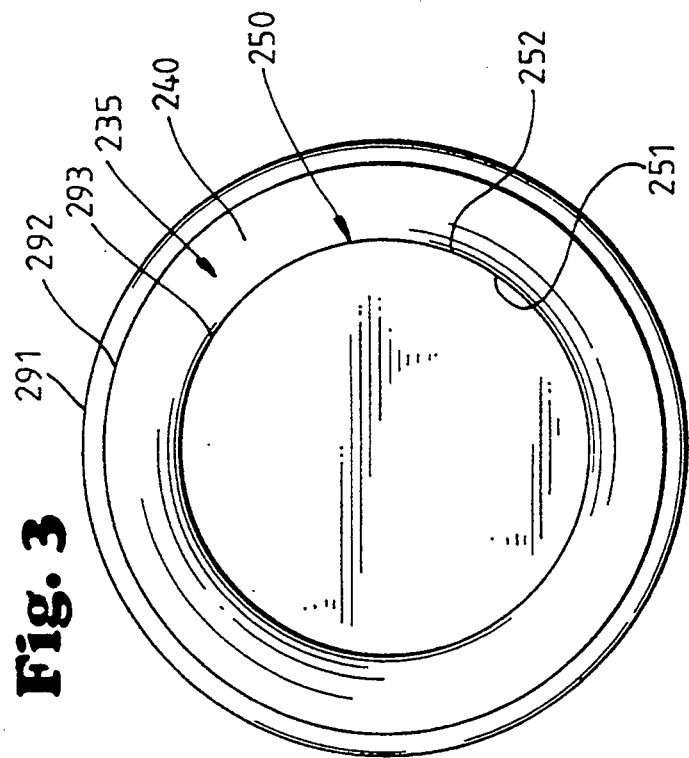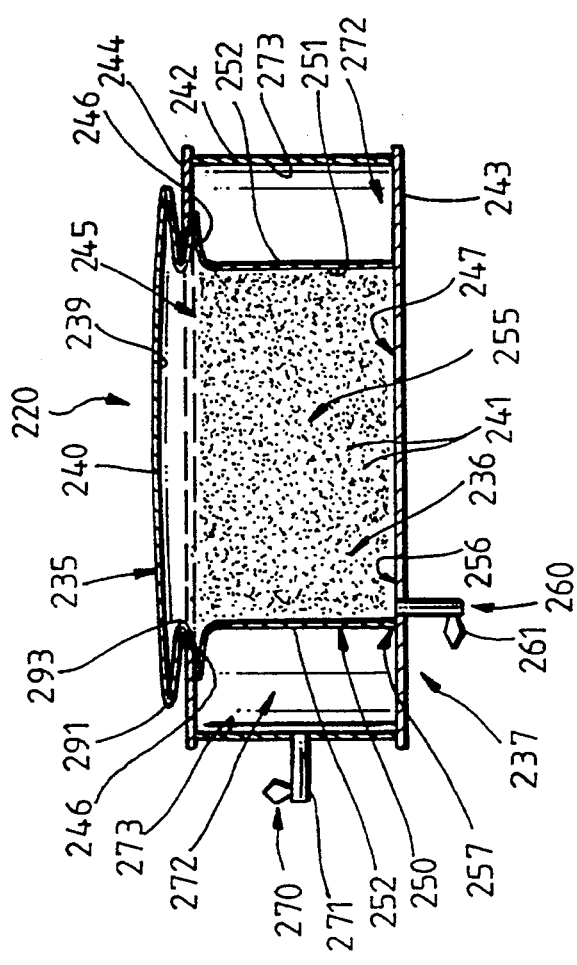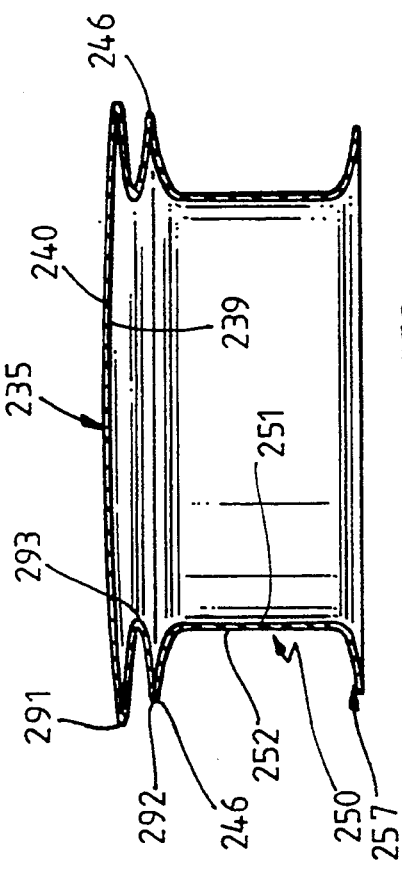

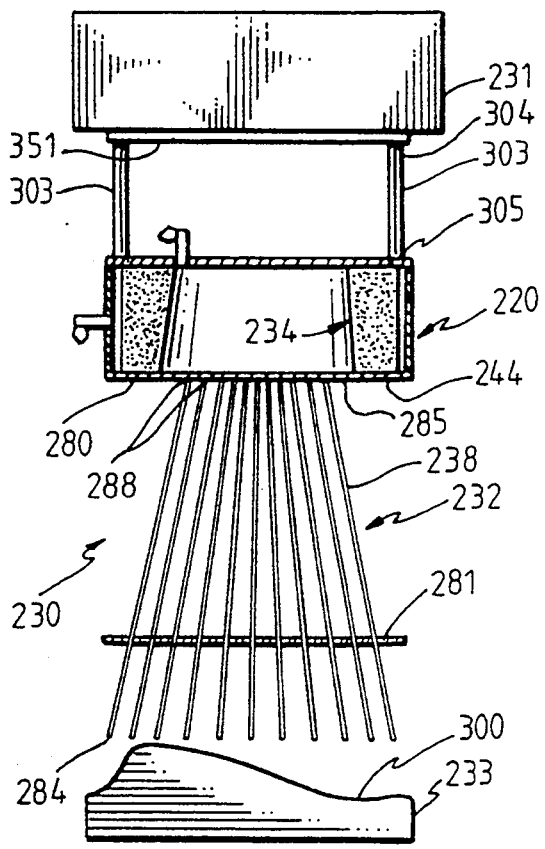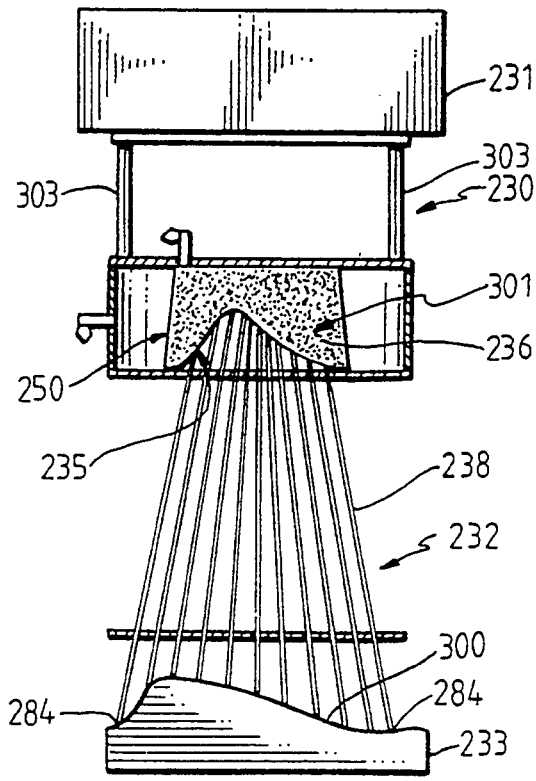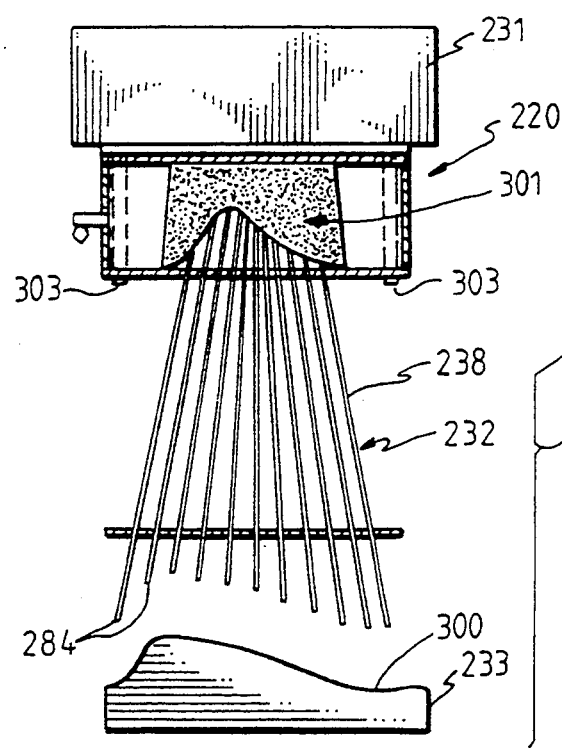

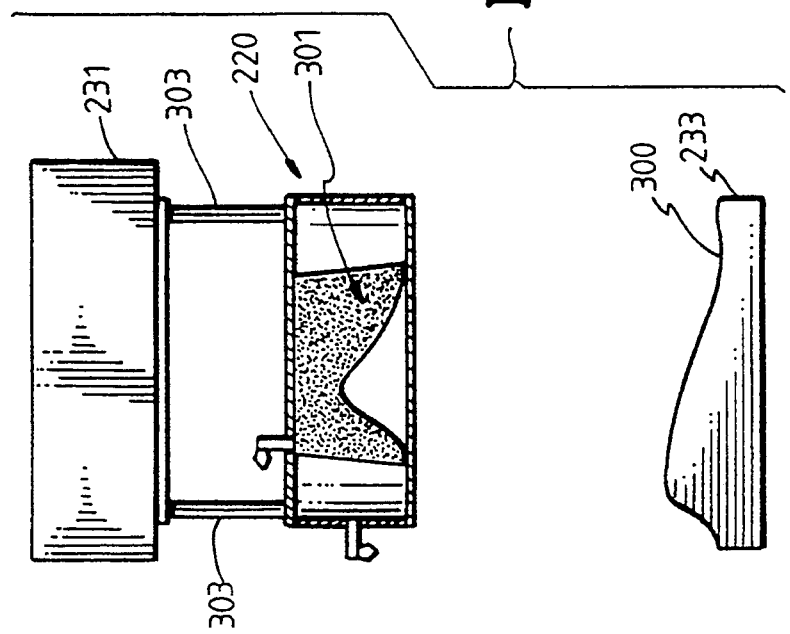
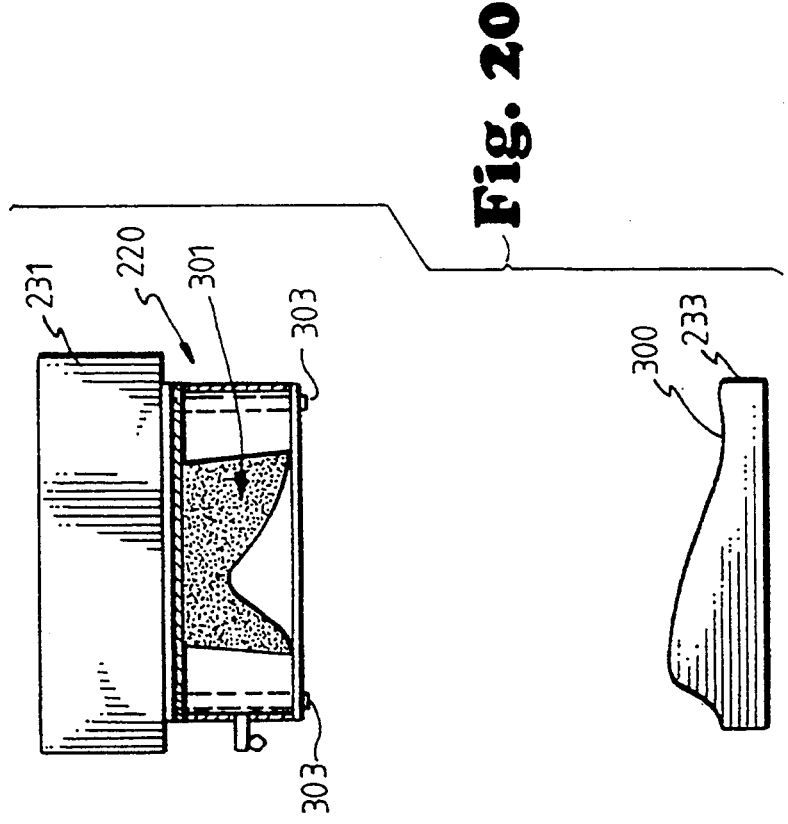

TISSUE COMPENSATION APPARATUS

This is a division, of application serial no. 07/791,041, filed Nov. 12, 1991 now U.S. Pat. No. 5,242,372.

BACKGROUND OF THE INVENTION

1. Field of the Invention

The invention relates to a tissue compensation system and method for use its with a linear accelerator to provide radiation therapy to a portion of a patient, whereby some of the radiation beam impinging on thinner areas of tissue within a treatment area are absorbed by the tissue compensator.

2. Description of the Prior Art

Many hospitals provide radiation therapy to their patients, particularly older patients for whom cancer has become an ever growing problem. An area which is of growing interest in the field of radiation therapy is that of tissue compensation, or the practice of absorbing some of the radiation beam impinging on thinner areas of tissue within a treatment area. Tissue compensation permits a higher effective dose of radiation to be delivered to thicker tissue areas without overdosing the areas of "missing" tissue, or the thinner areas of tissue. The difference in dosage that can be delivered can amount to as much as thirty percent depending upon the differences in thickness and the power of the linear accelerator employed to provide the radiation therapy.

Several systems are known which assemble varying thicknesses of metal compensatory blocks which are interposed in the path of the radiation treatment beam. This process usually involves two steps, wherein information is first obtained about the contour of the treatment surface on patient's body which is to be exposed to the radiation beam, which information indicates how much tissue is "missing" at any given spot on the contoured surface. In the second step, the information obtained is used to generate a tissue compensator, assembled from small blocks, employed at the time of patient treatment. In one system, patient contour information is obtained by reading the position of a tracing stylist directed on the patient's body as reflected in a magnetic field generated by a mechanism under the table upon which the patient rests. This contour information is fed to a three-axis CNC milling machine which is used to generate a compensatory pouring mold which is later filled with a metal alloy. At the end of the procedure the metal alloy is recovered and the styrofoam mold which has been prepared is discarded.

In another system, a light-dot pattern is projected on the treatment area on the contoured surface of the patient. The distortion of each light-dot is quantified by a computer, which then generates the information necessary to construct a compensator out of aluminum and brass blocks.

The foregoing systems have the disadvantages of: being very expensive; requiring sophisticated computer interfaces to obtain the necessary information relating to the contour of the treatment area on the patient's body; requiring valuable technician time to create the compensator; and requiring floor space, which is in sometimes short supply in a hospital or a radiation therapy center, to store the various components of the systems.

Another approach to obtaining information about the contour of a surface to be treated on the patient has been the use of a box containing a plurality of rods which can project outside the box. The box may be laid against the patient's body to indicate differences in tissue depth as a function of the location of the rod with respect to the box. The differences in tissue depth, or the differences in lengths of the rods once they are laid against the body, are then measured and that information is used to build a compensator. The disadvantages associated with the use of such a box include the following problems.

The basic problem is one of spatial resolution. The treatment area on a surface of the patient's body for which tissue compensation might be needed could extend over a square surface having outer dimensions of from 20 to 30 centimeters on some patients. In order to be of use to properly obtain information from which to prepare a tissue compensator, such boxes must have the capability of recording differences of tissue depth for every square centimeter on the treatment surface. For the maximum size treatment area previously described, it would then be necessary to use 400-900 rods for which the linear displacement of each rod extending out of the box would need to be measured and recorded. The time and physical manipulation necessary to measure and record the lengths of so many rods is prohibitive, and it is questionable as to whether or not it is even possible. Such prior art boxes did not include enough rods to be capable to record differences for every square centimeter on the treatment surface. In addition, the likelihood of introducing errors when one is to measure, record, and transfer such a quantity of information manually makes such an approach subject to errors, which could create substantial risks associated with the radiation therapy using compensator based upon such information.

Another disadvantage associated with such a prior art box is that the information obtained from measuring the displacement of the rods cannot be readily used as it is measured. The radiation beam exiting a point source at the head of the radiation therapy machine, such as a linear accelerator, is a divergent beam which spreads outwardly prior to striking the treatment surface on the patient. Accordingly, the compensation required at the head of the linear accelerator, where such compensators are mounted, is a compacted form of the actual measurements generated at the treatment surface of the patient. Such prior art boxes including a plurality of rods measured the rod displacement in a plane perpendicular to the treatment sur#ace. Accordingly, it would be necessary to take into consideration the divergent nature of the ,radiation beam, as it affects measurements obtained from such a prior art box, and such prior art boxes did not take this factor into account.

Accordingly, prior to the development of the present invention, there have been no tissue compensation methods and apparatus which: are simple to understand and easy and economical to use; sensitive enough to permit depth information to be obtained for every square centimeter on the patient's treatment surface; take into account the diverging nature of the radiation beam; require as little transfer of data as possible, so as to minimize the chance of introduction of measurement errors; do not require any ancillary equipment such as computers, milling machines, etc., all of which add additional costs in terms of money, space, and personnel requirements; and respect the environment by not utilizing disposable components and permit all parts to be reused.

Therefore, the art has sought a tissue compensation method and apparatus which: are simple to understand and easy and economical to use; are sensitive enough to obtain tissue depth information for every centimeter on the treatment surface; account for the diverging nature of the radiation treatment beam; require as little data as possible, so as to minimize the chance of the introduction of errors; do not require any ancillary equipment such as computers, milling machines, etc., so as to not add any additional cost in terms of money, space, and personnel requirements; and are respectful of the environment by not requiring the use of disposable components and permit all of its components to be reused.

SUMMARY OF THE INVENTION

In accordance with the invention, the foregoing advantages have been achieved through the present tissue compensation system for use with a linear accelerator to provide radiation therapy to a portion of a patient. The present invention includes: a plurality of elongate rods, each rod having a longitudinal axis and first and second ends, the first ends adapted to contact the surface on the patient adjacent to the portion of the patient to receive the radiation therapy, the rods being mounted for movement in a direction along their longitudinal axes, and at least some of the rods being moved, upon the first ends of some of the rods contacting the patient; a compensator housing, the housing including a first membrane, which is flexible and deformable and has an inner and an outer surface and contains a quantity of a material substantially equivalent to tissue of the patient; at least some of the second ends of the elongate rods being disposed to contact the outer surface of the first membrane and to deform the membrane and the tissue equivalent material in response to movement caused by at least some of the first ends of the elongate rods contacting the patient, whereby the tissue equivalent material is disposed in a spatial relationship within the compensator housing to absorb some of the radiation from the radiation therapy upon a radiation beam passing through the compensator housing.

Another feature of the present invention is that there may be provided a means for retaining the shape of the first membrane after the first membrane has been deformed by at least some of the second ends of the elongate rods, and the shape retaining means may include a first means for creating a vacuum in the compensator housing, whereby the first membrane may be retained in the deformed shape by the vacuum and the inner surface of the first membrane bears against the tissue equivalent material. A further feature of the present invention is that the tissue equivalent material may be a plurality of small diameter beads disposed within the compensator housing, which beads may be formed of polystyrene plastic.

An additional feature of the present invention is that the compensator housing may include a second membrane disposed therein, which is flexible and deformable, and has an inner and an outer surface. Another feature of the present invention is that the compensator housing has an interior surface, and the tissue equivalent material may be disposed within a first cavity defined by the inner surfaces of the first and second membranes and at least a first portion of the interior surface of the compensator housing. Another feature of the present invention is that the first and second membranes may be formed integral with each other.

A further feature of the present invention is that the first means for creating a vacuum in the compensator housing may be in fluid communication with the first cavity defined by the inner surfaces of the first and second membranes and at least the first portion of the interior surface of the compensator housing, and a second means for creating a vacuum in the compensator housing may be provided and is in fluid communication with a second cavity in the compensator housing, which cavity is defined by the outer surface of the second membrane and at least the second portion of the interior surface of the compensator housing.

An additional feature of the present invention is that the plurality of rods may be disposed in a rod framework which includes an upper and a lower plate member, the plate members being spaced apart from each other, and each plate member may have a plurality of openings formed therein to which the plurality rods pass. A further feature of the present invention is that the second ends of the plurality of rods may each have an abutment member associated therewith and are adapted for engagement with the upper plate member to prevent the plurality of rods from completely passing through the openings formed in the upper plate member. Another feature of the present invention is that the upper and lower plate members may be disposed in a substantial parallel relationship with each other and a substantial number of the plurality of elongate rods may be disposed with their longitudinal axes disposed in a non-perpendicular angular relationship with the upper and lower plate members.

In accordance with another aspect of the invention, the foregoing advantages have also been achieved through the present method for making a tissue compensator for use with a linear accelerator to provide radiation therapy to a portion of a patient. This aspect of the present invention includes the steps of: disposing a plurality of rods, each rod having a longitudinal axis and first and second ends, above the portion of the patient to be treated; disposing a compensator housing above the plurality of rods; contacting a surface on the patient, adjacent to the portion of the patient to be treated, with at least some of the first ends of the plurality of rods to cause movement of at least some of the rods in a direction along their longitudinal axes; contacting a first membrane associated with the compensator housing with the second ends of the rods which have moved, the first membrane being flexible and deformable and has an inner and an outer surface and contains a quantity of a material which is substantially equivalent to tissue of the patient; and deforming the first membrane and the tissue equivalent material in response to the movement of the rods, whereby the tissue equivalent material is disposed in a spatial relationship within the compensator housing to absorb some of the radiation from the radiation therapy upon a radiation beam passing through the compensator housing.

A further feature of the present invention may include the step of retaining the shape of the first membrane after the first membrane has been deformed by at least some of the second ends of the elongate rods, and the shape of the first membrane may be retained by creating a vacuum in the compensator housing. Another feature of the present invention may include the step of utilizing a plurality of small diameter beads as the tissue equivalent material, and the beads may be formed of polystyrene plastic.

A further feature of the present invention includes the steps of: disposing a second membrane, which is flexible and deformable and has an inner and an outer surface, within the compensator housing; and disposing some of the tissue equivalent material in contact with the interior surface of the second membrane. An additional feature of the present invention is that the compensator may have an inner surface, and the tissue equivalent material is disposed in the first cavity defined by the inner surfaces of the first and second membranes in at least a first portion of the interior surface of the compensator housing. Another feature of the present invention may be the step of forming the first and second membranes integral with each other. A further feature of the present invention may include the step of disposing the first means for creating a vacuum in the compensator housing in fluid communication with the first cavity defined by the inner surfaces of the first and second membranes and at least a first portion of the interior surface of the compensator housing.

An additional feature of the present invention may include the step of disposing a second means for creating a vacuum in the compensator housing in fluid communication with a second cavity in the compensator housing defined by the outer surface of the second membrane and at least a second portion of the interior surface of the compensator housing. Another feature of the present invention may include the steps of: disposing the plurality of rods in a rod framework which includes an upper and a lower plate member; spacing the plate members apart from each other; forming a plurality of openings in each of the plate members; and passing each of the plurality of rods through an opening in the upper and lower plate member. A feature of the present invention may include the steps of: disposing an abutment member, on the second end of each of the plurality of rods, for engagement with the upper plate member to prevent the plurality of rods from completely passing through the openings formed in the upper plate member.

A further feature of the present invention may include the steps of: disposing the upper and lower plate members in a substantially parallel relationship with each other; and disposing a substantial number of the plurality of elongate rods with their longitudinal axes in a non-perpendicular angular relationship with the upper and lower plate members. Another feature of the present invention may include the step of selectively positioning the compensator housing in at least two positions with respect to the linear accelerator, whereby the compensator housing may be positioned adjacent to the linear accelerator or in an offset spaced relationship therefrom.

In accordance with another aspect of the invention, the foregoing advantages have been achieved through the present method of making a tissue compensator for use with a linear accelerator to provide radiation therapy to a treatment surface on a patient, the treatment surface having a varying contour. This aspect of the invention includes the steps of: disposing a membrane, which is flexible and deformable and contains a quantity of material which is substantially equivalent to tissue of the patient, beneath the linear accelerator; disposing the patient beneath the membrane; disposing a plurality of movable rods between the patient; and contacting the contoured surface on the patient and the membrane with the plurality of rods to deform the membrane and the tissue equivalent material to dispose the tissue equivalent material within the membrane in a spatial relationship corresponding to the contour of the surface on the patient. Another feature of the present invention may include the step of disposing the plurality of rods in a downwardly and outwardly sloping relationship between the membrane and the patient.

The tissue compensation system and method of the present invention, when compared with previously proposed prior art methods and apparatus, have the advantages of: being simple to understand and easy and economical to use; are sensitive enough to provide information for every square centimeter of the patient treatment surface; take into account the diverging nature of the radiation treatment beam; require no transfer of data, so as to minimize the likelihood of introduction of errors into the tissue compensator; do not require any ancillary equipment, such as computers, milling machines, etc., and thus does not add any additional costs because of equipment, space, and personnel requirements; and are respectful of the environment, in that there are no disposables used and all of the components are capable of being reused.

BRIEF DESCRIPTION OF THE DRAWINGS

In the drawings:

FIG. 1 is a partial cross-sectional view of a tissue compensator housing in accordance with the present invention;

FIG. 2 is a side view of a membrane component of the tissue compensator housing of FIG. 1;

FIG. 3 is a top view of the membrane of FIG. 2;

FIGS. 17-21 are partial cross-sectional views of the tissue compensation system, in accordance with the present invention, illustrating the steps for making a tissue compensator.

Figure 5:
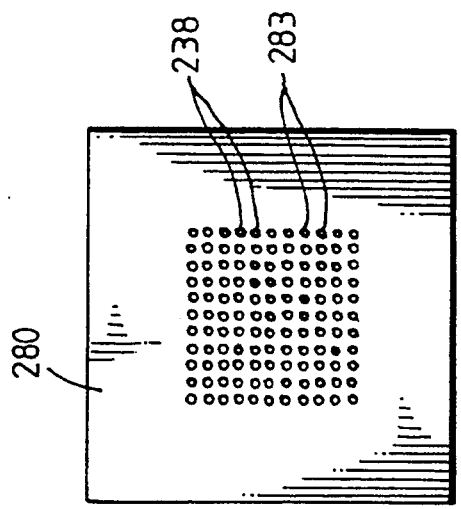
FIG. 5 is a top view of the rod framework of FIG. 4.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

With reference to FIGS. 1-3, a tissue compensator housing 220, in accordance with the present invention, which forms a part of the tissue compensation system 230 (FIGS. 17-21) of the present invention for use with a linear accelerator 231 (FIGS. 17-21) and a rod framework 232 (FIGS. 4-6) to provide radiation therapy to a portion of a patient 233 (FIGS. 17-21) generally includes: a first membrane 235; a quantity of material 236 substantially equivalent to tissue of the patient disposed within the first membrane 235; and means for retaining 237 the shape of the first membrane 235 after the first membrane 255 has been deformed by at least some elongate rods 238 (FIGS. 4-6) as will be hereinafter described in greater detail. The first membrane 235 of tissue compensator housing 220, is flexible and deformable and has an inner and an outer surface 239, 240, and has a generally circular configuration as seen in FIG. 3, although as will be readily apparent to one of ordinary skill in the art, first membrane 235 could have other configurations. First membrane 235 must also be liquid tight as will also be hereinafter described in greater detail. First membrane 235 may be formed of any suitable flexible and deformable material, such as latex rubber, synthetic rubber, coated nylon fabric, or any other suitable material having the requisite flexibility and fluid tight characteristics necessary for first, or outer, membrane 235 to function as will hereinafter be described. Tissue equivalent material 236 may be a plurality of small diameter beads 241 which have substantially the same resistance to radiation as does normal human tissue. Preferably the beads 241 are formed of polystyrene plastic. Tissue equivalent material 236 could be any material which has substantially the same resistance to radiation, or radiation absorptive characteristics, as does normal human tissue, which material 236 is capable of being moved within tissue compensator housing 220 upon an application of force upon the outer surface 240 of first membrane 235.

Figure 14:
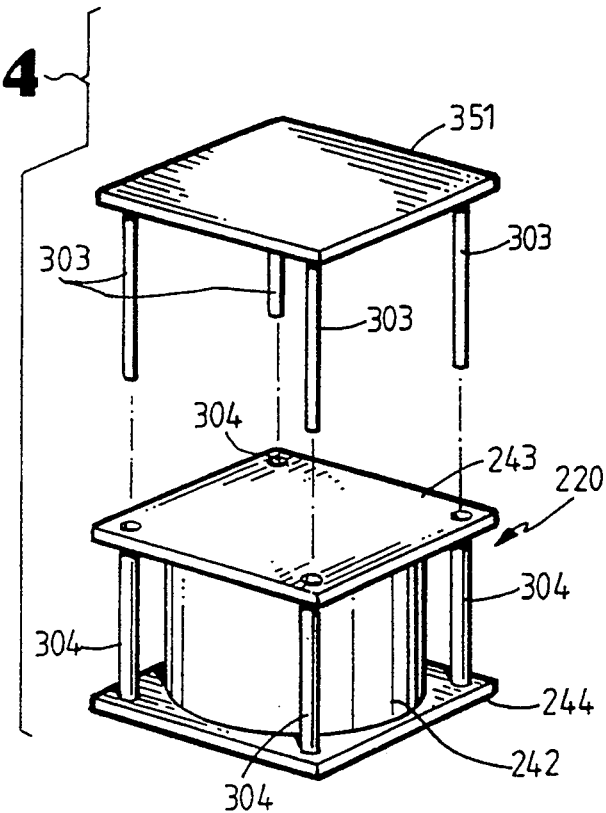
FIG. 14 is a perspective view of the adjustable mounting means of FIG. 13.
Figure 13:
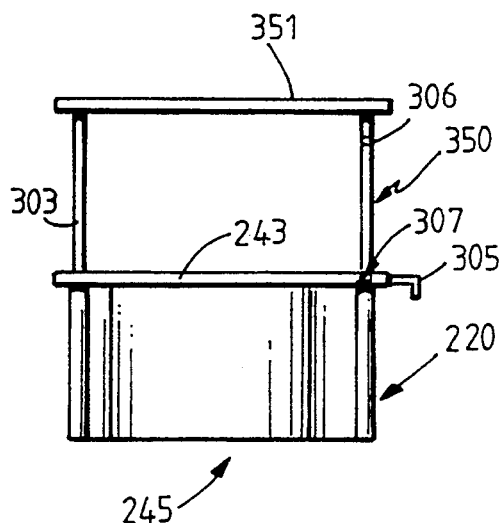
FIG. 13 is a side view of a means for adjustably mounting the tissue compensator housing of FIG. 1 to a linear accelerator.
Figure 15:
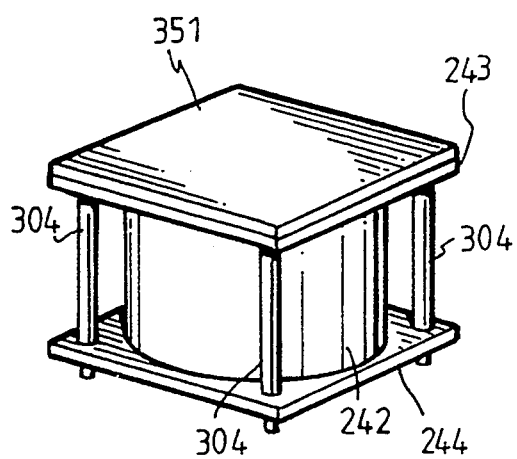
FIG. 15 is a perspective view of the adjustable mounting means of FIG. 13 in its retracted position.
Figure 16:
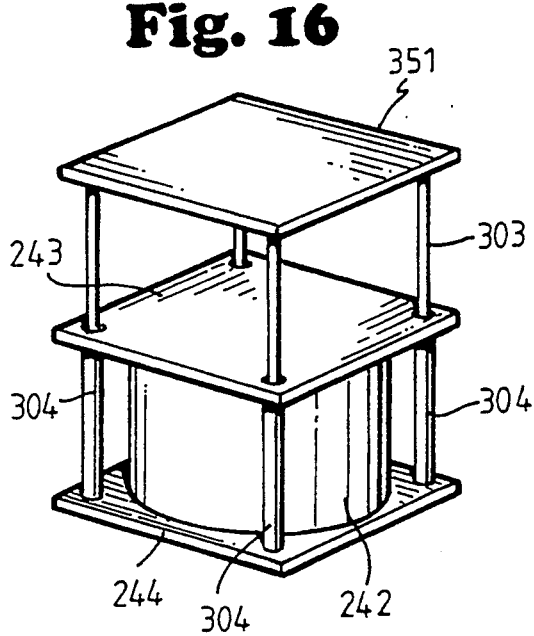
FIG. 16 is a perspective view of the adjustable mounting means of FIG. 13 illustrating its extended position.

Still with reference to FIGS. 1-3, compensator housing 220 may preferably include a tubular shaped outer wall 242, when viewed from the top, sealed at its lower end by a lower sealing plate 243 having a square configuration, as seen in FIGS. 14-16. A square shaped upper sealing plate 244 is provided; upper sealing plate 244 having a circular shaped opening 245 formed therein to permit first membrane 235 to enter compensator housing 220 as will be hereinafter described. Upper and lower sealing plates 244, 243 are preferably formed of a radiolucent material, as is first membrane 235, so that only tissue equivalent material 236 will absorb any radiation from linear accelerator 231. Upper and lower sealing plates 244, 243 may be joined to outer wall 242 in any conventional manner. O-rings (not shown) may be utilized to seal first membrane 235 where it joins upper sealing plate 244, as at 246. Compensator housing 220 has an interior surface 247, disposed along the interior surfaces of outer wall member 242 and upper and lower sealing plates 244, 243.

Compensator housing 220 may also include a second membrane 250 disposed within compensator housing 220, and second membrane 250 is flexible and deformable and has an inner and outer surface 251, 252. As seen in FIG. 1, tissue equivalent material 236 is disposed within a first cavity 255, which cavity 255 is defined by the inner surfaces 239, 251 of the first and second membranes 235, 250, and at least a first portion 256 of the interior surface 247 of compensator housing 220. Second membrane 250 is preferably formed of the same material as first membrane 235, and may be sealingly disposed within compensator housing 220 as by o-rings (not shown) at location 246 in upper sealing plate 244 and at location 257 with respect to lower sealing plate 243. Preferably, first and second membranes 235, 250 are formed integral with each other in the shape illustrated in FIG. 2, although two separate membranes could be utilized.

As seen in FIG. 1, shape retaining means 237 includes a first means, or creating a vacuum 260 in the compensator housing 220, for valve 261, in fluid communication with the first cavity 255 defined by the inner surfaces 239,251 of the first and second membranes 235, 250 and at least a first portion 256 of the interior surface 247 of the compensator housing 220. In addition to first vacuum creating means 260, a second means for creating a vacuum 270 may be provided. Second vacuum creating means 270, or valve 271, is in fluid communication with a second cavity 272 in compensator housing 220, which cavity 272 is defined by the outer surface 252 of the second membrane 250 and at least a second portion 273 of the interior surface 247 of the compensator housing 220. The second portion of the interior surface 273 is generally the interior surface of outer wall member 242 and the inner surfaces of upper and lower sealing plates 244, 243, which are disposed between the interior surface of outer wall member 242 and the outer surface 252 of second membrane 250. The operation of compensator housing 220 will be hereinafter described in greater detail in connection with FIGS. 7-12.

Figure 6:
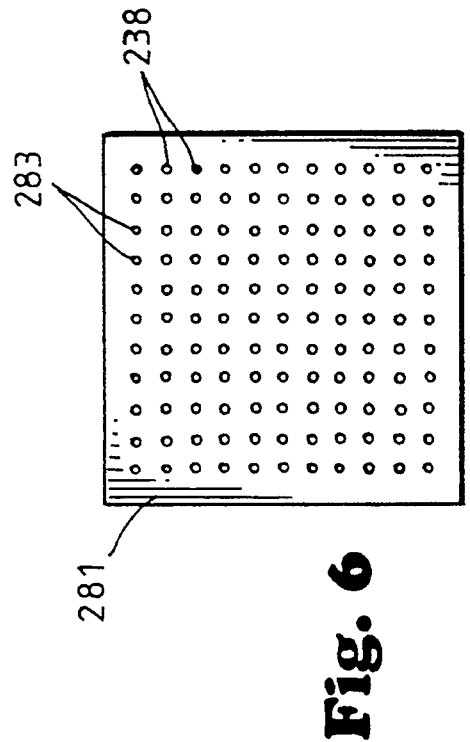
FIG. 6 is a bottom view of the rod framework of FIG. 4.
Figure 4:
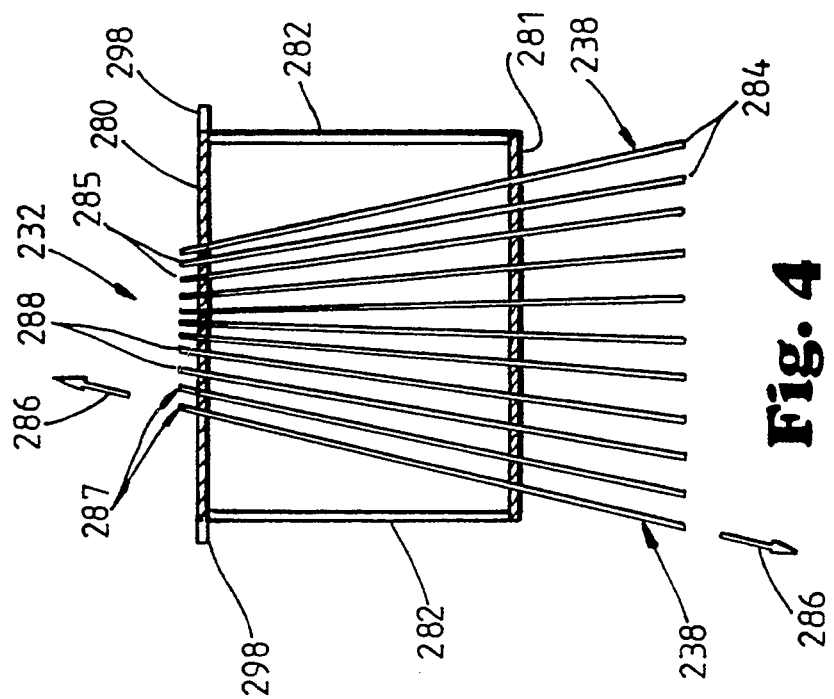
FIG. 4 is a side view of a rod framework in accordance with the prevent invention.

With reference to FIGS. 4-6, rod framework 232 for use with a linear accelerator 231 (FIGS. 17-21) and compensator housing 220 to provide radiation therapy on a portion of a patient 233 (FIGS. 17-21) generally includes: a plurality of elongate rods 238 and an upper and a lower plate member 280, 281, the plate members 280, 281 being spaced apart from each other as by connector plates 282, and each plate member 280, 281 has a plurality of openings 283 formed therein through which the plurality of rods 238 pass. Elongate rods 238 may be formed of any suitable metal or plastic material having the requisite rigidity requirements to function as hereinafter described. Each rod 238 has a longitudinal axis and first and second ends 284, 285. The rods 238 are mounted for movement in a direction along their longitudinal axes as shown by arrows 286 (FIG. 4), with the first ends 284 adapted to contact a surface on the patient 233 (FIGS. 17-21) who is to receive the radiation therapy, as will be hereinafter described in connection with FIGS. 17-21, and at least some of the second ends 285 of the elongate rods 238 being disposed and adapted to contact the compensator housing 220 as will be hereinafter described in connection with FIGS. 7-12.

Still with reference to FIGS. 4-6, the second ends 285 of the plurality of rods 238 are preferably provided with an abutment member 287, or flange member or spur 288, which are adapted for engagement with the upper plate member 280, as seen in FIG. 17, to prevent the plurality of rods 238 from completely passing through the openings 283 formed in the upper plate member 280. As seen in FIG. 4, the upper and lower plate members 280, 281 are disposed in a substantially parallel relationship with each other. A substantial number of the plurality of the elongate rods 238 are disposed with their longitudinal axes disposed in a non-perpendicular angular relationship with respect to the upper and lower plate members 280, 281, in order to take into consideration the diverging nature of the radiation beam from linear accelerator 231, as will be hereinafter described in greater detail. In general, the elongate rods 238 are disposed in a downwardly and outwardly sloping relationship from the upper plate member 280 to the lower plate member 281.

Figure 7:
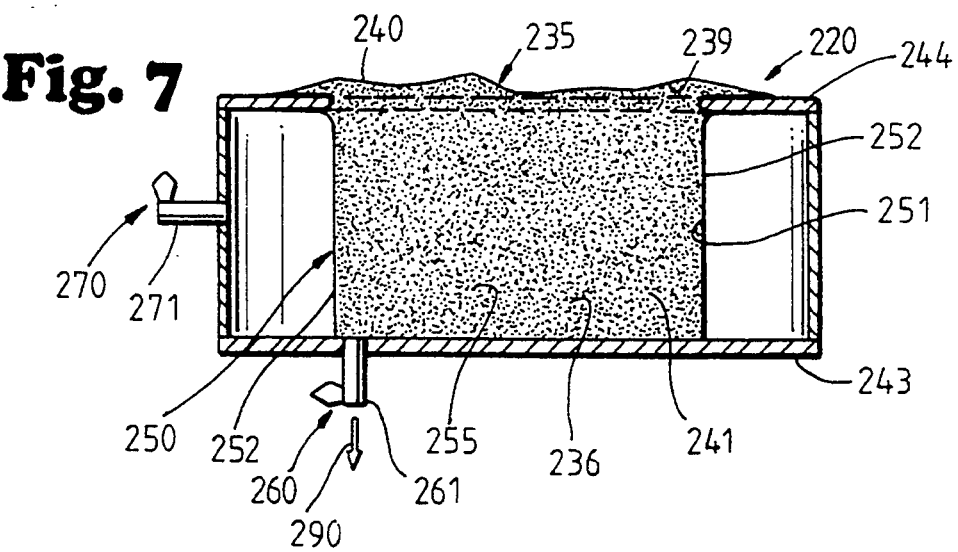
FIGS. 7-12 are partial cross-sectional views of the tissue compensator housing of FIG. 1, illustrating the operation of the tissue compensator housing of FIG. 1.

The openings 283 formed in the lower plate member 281 are spaced on approximately one centimeter centers, to permit the first ends 284 of elongate rods 238 to generally contact every square centimeter of portion of patient 233 as will be hereinafter described in greater detail. For example, if the treatment surface 300 (FIG. 17) of the patient is approximately a square shaped area measuring 20 by 20 centimeters, the treatment surface 300 would have 400 square centimeters of area and would require 400 elongate rods 238. For ease of illustration, that number of rods 238 and corresponding openings 283 have not been illustrated. Because of the downwardly and outwardly sloping relationship of elongate rods 238 from the upper plate member 280 to the lower plate member 281, openings 283 in upper plate member 280 are spaced on centers somewhat less than one centimeter as illustrated in FIG. 5. The actual distance between openings 283 in upper plate member 280, and the corresponding angular relationship of rods 238 with respect to upper and lower plate member 280 and 281 is readily determined by the specific divergence angle of the radiation beam for any given linear accelerator 231. The spacing between upper and lower plate members 280, 281 determined by the length of connecting members 282 is also dependent upon the known, specific divergence angle for the linear accelerator 231 with which rod framework 232 is utilized.

with reference to FIGS. 7-12, the operation of compensator housing 220 will be described. In FIG. 7, first vacuum creating means 260, or valve 261, is opened, and the first membrane, or outer membrane, 235 is pressed downwardly to the configuration shown in FIG. 7, whereby the tissue equivalent material 236 completely fills first cavity 255, which cavity 255 is defined by the inner surfaces 2,39, 251 of the first and second, or outer and inner, membranes 235, 250. The first, or outer, membrane 235 thus lays upon the tissue equivalent material 236, and the only air present within first cavity 255, other than that present between the plurality of beads 241, exits first cavity 255 in the direction shown by arrow 290 from valve 261, at which time valve 261 is closed.

Figure 8:
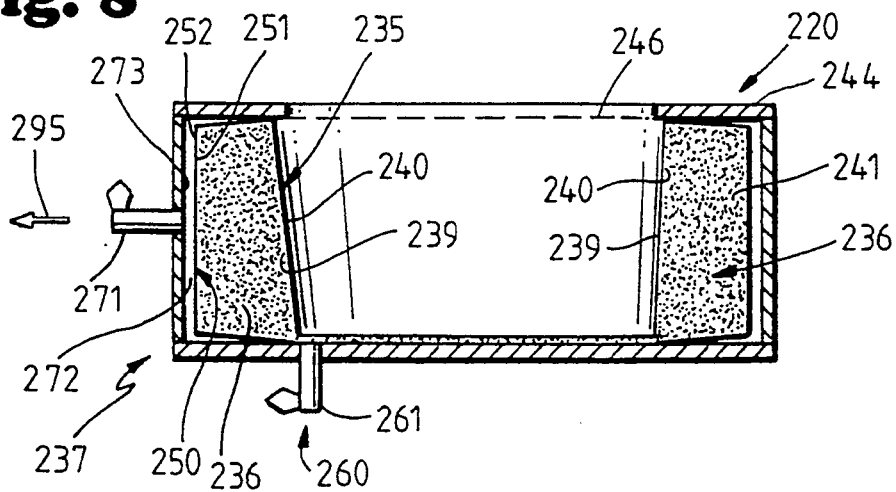

With reference to FIG. 8, second vacuum creating means 270, or valve 271 is opened, while valve 261 is closed, and a conventional vacuum pump (not shown) is connected to valve 271 to draw air outwardly of second cavity 272 in the direction of arrows 295, second cavity 271 being defined by the outer surface 252 of the second, or inner, membrane 250 and at least a second portion 273 of the interior surface 247 of the compensator housing 220. When the vacuum is applied to the second cavity 272, the tissue equivalent material 236 and first and second, or outer and inner, membranes 235, 250 assume the configuration illustrated in FIG. 8, with the outer membrane 235 having been sucked into compensator housing 220 through opening 245 in the upper sealing plate 244 of compensator housing 220. After compensator housing 220 has assumed the configuration illustrated in FIG. 8, valve 271 is closed, while valve 261 remains in its previously closed position. In this regard, it should be noted that as seen in FIGS. 1-3, first membrane 235 is of sufficient size, because of folds 291, 292, and 293, and has extra material available to permit first, or outer, membrane 235 to assume its disposition illustrated in FIG. 8.

Figure 9:
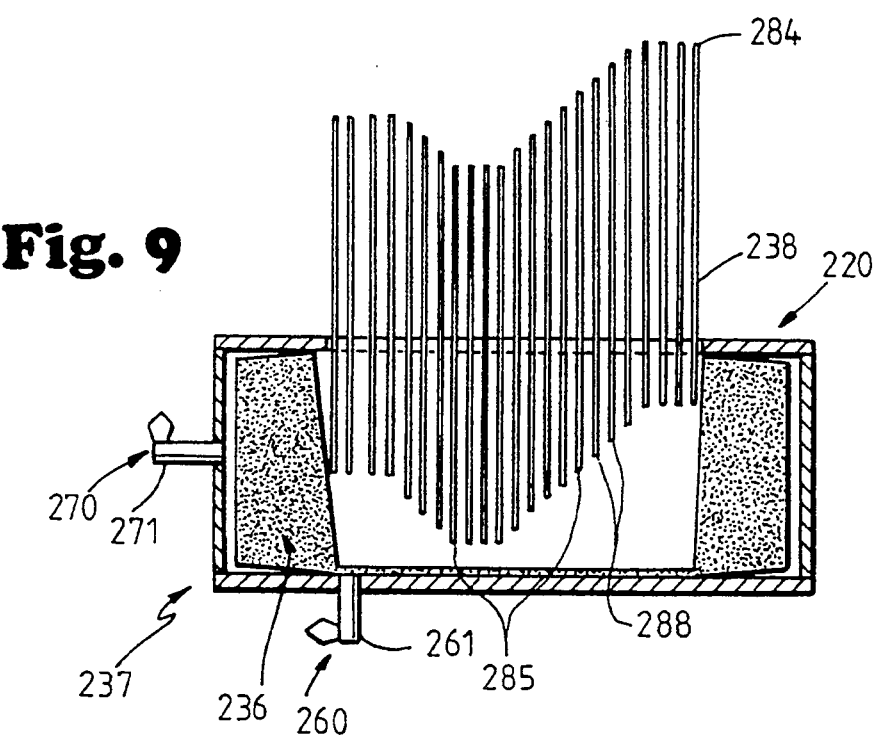
Figure 10:
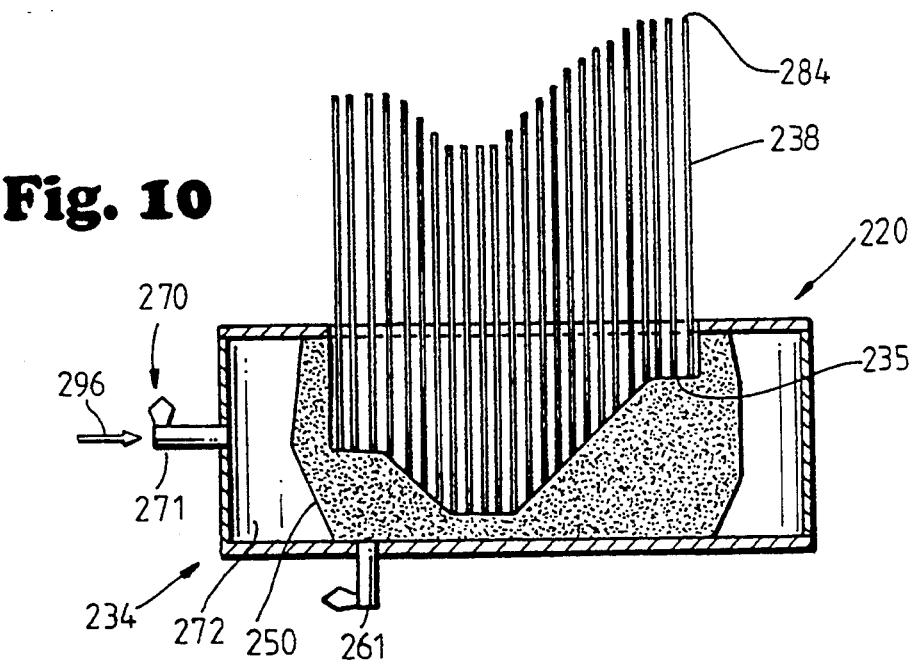

With reference to FIG. 9, the second ends 285 of the plurality of rods 238 are caused to enter compensator housing 220 as will be hereinafter described in connection with FIGS. 17-21, while valves 271 and 261 remain closed, with tissue equivalent material 236 and first and second membranes 235, 250 remaining in the configuration illustrated in FIG. 8. With reference to FIG. 10, second vacuum creating means 270, or valve 271, is then opened permitting air to flow into second cavity 272 in the direction of arrow 296, whereby the flexible second, or inner, membrane 250 springs back to the configuration illustrated in FIG. 10, whereby second membrane 250 acts upon tissue equivalent material 236, to in turn cause first, or outer, membrane 235 to assume a closely conforming configuration about the second ends 285 of rods 238 as illustrated in FIG. 10.

Figure 11:
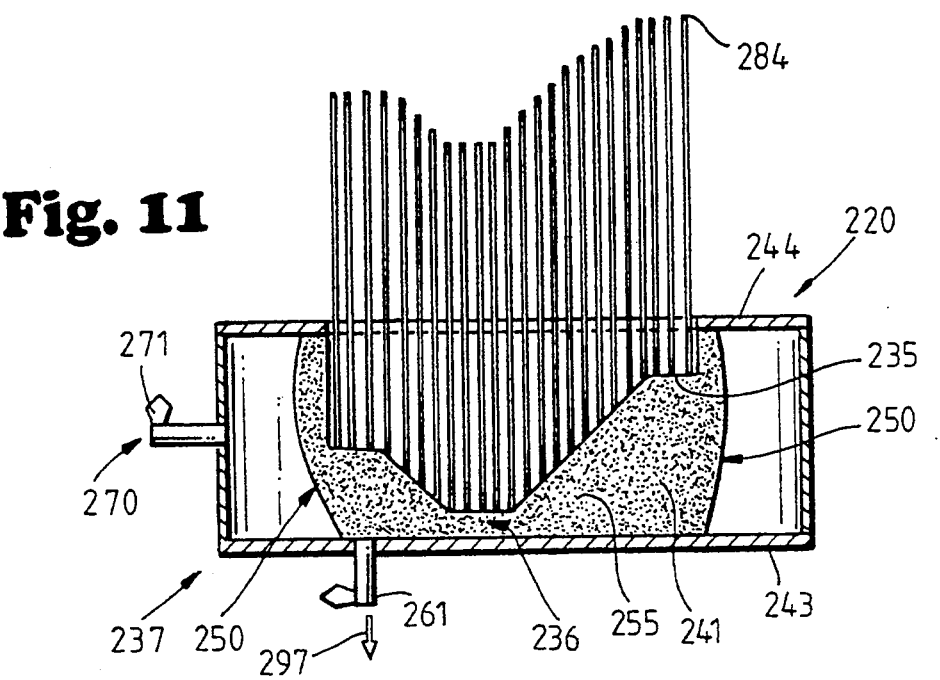
Figure 12:
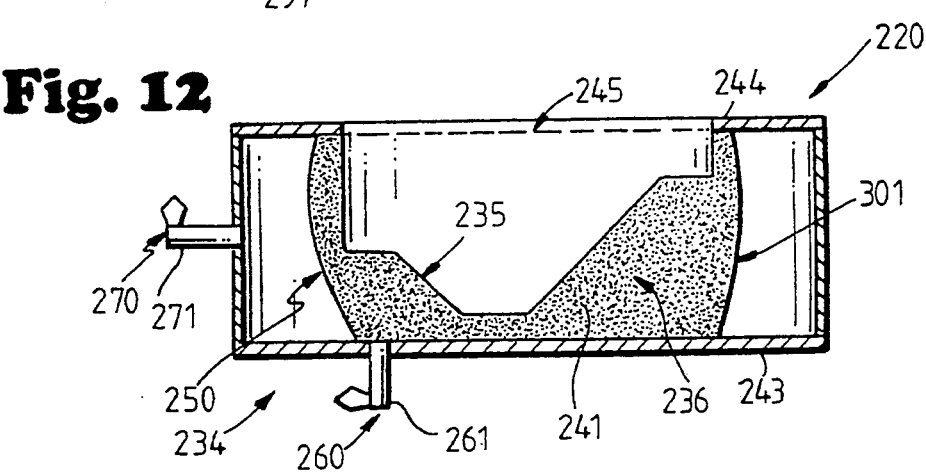

Turning to FIG. 11, valve 271 is maintained in an open position, and valve 261 is opened and a vacuum pump is connected to valve 261 to cause air to be sucked outwardly of first cavity 255 in the direction of arrows 297. The vacuum is maintained in first cavity 255, until all the air therein has been evacuated, whereby second, or outer, membrane 250 is sucked inwardly into the configuration illustrated in FIG. 11, thus compressing the plurality of beads 241 of tissue equivalent material 236 into a closely conforming relationship with the second ends 285 of rods 238. Upon closing valve 261, the vacuum in first cavity 255 serves to restrain, and prevent, any further movement of beads 241 caused by the deformation of first, or outer, membrane 235 caused by second ends 285 of rods 238 contacting outer membrane 235. The tissue equivalent material 236, or beads 241, are thus "frozen" into the configuration illustrated in FIG. 11. As illustrated in FIG. 12, upon the removal of rods 238 from compensator housing 220, and valves 261, 271 remaining closed, the desired tissue compensator 301 has been made, and may be used as hereinafter described with a linear accelerator 231 to provide radiation therapy to a patient.

Turning now to FIGS. 17-21, the method for making a tissue compensator 301, and a tissue compensation system 230, in accordance with the present invention, will be described. As illustrated in FIG. 17, a linear accelerator 231 of conventional design is shown to be disposed above a portion of a patient 233 having a treatment surface 300 thereon which has a varying contour. Compensator housing 220 is mounted to the linear accelerator 231, as by alignment tubes 303 which are secured at their upper ends 304 to linear accelerator 231, and at their lower ends 305 to compensator housing 220. It should be noted that compensator housing 220 is disposed beneath linear accelerator 231 in an inverted position from that illustrated in FIGS. 1 and 7-12, whereby upper sealing plate 244 and first, or outer membrane 235 face treatment surface 300. Prior to mounting compensator housing 220 to linear accelerator 231, compensator housing 220 has had a vacuum applied to it as previously described in connection with FIGS. 7 and 8, whereby first and second, or outer and inner membrane 235, 250 have assumed the configuration illustrated in FIG. 8, at which time compensator housing 220 is attached to linear accelerator 231. Alternatively, the steps previously described in connection with FIGS. 7 and 8 are performed while compensator housing 220 is attached to linear accelerator 231.

Rod framework 232 is then releasably mounted to compensator housing 220, as by releasably mounting the upper plate 280 of rod framework 232 to the upper sealing plate 244 of compensator housing 220 in any conventional manner, as by locknuts, thumb screws, or by sliding upper plate member 280 into a mating groove provided in upper sealing plate 244. In this regard, upper plate member 280 of rod framework 232 may be provided with outwardly extending flange members 298 (FIG. 4) which may slide into a mating groove provided in the upper sealing plate 244 of compensator housing 220. For ease of illustration, connecting members 282 (FIG. 4) of rod framework 232 have not been shown in FIGS. 17–21.

Turning to FIG. 18, either linear accelerator 231 and compensator housing 220 are lowered, or the portion of patient 233 with treatment surface 300 thereon is raised, whereby at least some of the first ends 284, and preferably all the first ends 284 of the plurality of rods 238 contact treatment surface 300. Because of the varying contour of treatment surface 300 at least some of the rods. 238 are caused to move in a direction along their longitudinal axes. The movement of the elongate rods 238 causes the second ends 285 of elongate rods 238 to enter compensator housing 220 in a manner previously described in connection with FIG. 9. Upon valve 271 being opened as previously described in connection with FIG. 10, and a vacuum created in first cavity 255 as previously described in connection with FIG. 11, tissue equivalent material 236 is disposed in a spatial relationship within compensator housing 220 to form a tissue compensator 301, as illustrated in FIG. 18. Tissue compensator 301 may thus function to absorb some of the radiation from the radiation therapy upon a radiation beam passing through the tissue compensator 301 in compensator housing 220.

Because it is important to maintain a precise spatial relationship between linear accelerator 231, tissue compensator 301, and treatment surface 300 of the patient, it is desirable to not move the patient away from linear accelerator 231 and tissue compensator 301 disposed within compensator housing 220. As illustrated in FIG. 19, compensator housing 220 is raised from treatment surface 300, after which elongate rods 138 slide downwardly until abutment members 287 contact the upper plate member 280 of rod framework 232. As illustrated in FIG. 20, rod framework may then be removed from compensator housing 220, which results in tissue compensator 301 and compensator housing 220 being disposed in the configuration illustrated in FIG. 20.

Turning to FIG. 21, compensator housing 220 may then be lowered with respect to linear accelerator 231, resulting in tissue compensator 301 being disposed with respect to treatment surface 300 in the exact position it had at the time tissue compensator 301 was made, as described in connection with FIG. 18. Linear accelerator may then be activated to provide the desired radiation therapy upon treatment surface 300, whereby radiation beams emanating from linear accelerator 231 pass through tissue compensator 301 which absorbs some of the radiation from linear acceleration 231 before the radiation strikes the treatment surface 300.

It should be noted that the displacement of the elongate rods 238 along their longitudinal axes at their interface with treatment surface 300, as illustrated in FIG. 18, will cause the desired displacement of the second ends 285 at their interface with first membrane 235, when contacting and deforming first, or outer membrane 235. The displacement at the interface between the second ends 285 and the first membrane 235 will be equal in length to that caused perpendicular to the interface between the treatment surface 300 and the first ends 284 of rods 238. However, the displacement at the interface between the second ends 285 of rods 238 and first membrane 235 will be compacted in the plane parallel to that interface. The degree of compaction is dependent upon the relative spacings of the openings 283 in the upper plate member 280 with respect to the spacings between the opening 283 in the lower plate member 281 as previously described in connection with FIGS. 4–6. This compaction thus accounts for the diverging nature of the radiation beam originating in linear accelerator 231, as the radiation beam travels downwardly to contact treatment surface 300.

Turning to FIGS. 13–16, a mounting means 350 for compensator housing 220 is illustrated which provides for the previously described relative movement and selective positioning of compensator housing 220 with respect to linear accelerator 231. Mounting mean 350 generally includes a square-shaped mounting plate member 351, and the mounting plate member 351 may be fixedly secured to linear accelerator 231 in any conventional manner, as illustrated in FIG. 17. Compensator housing 220 may be provided with four alignment tubes 304 which telescopically receive, and mate with, alignment tubes 303 depending from mounting plate member 351. Alignment tubes 304 are fixedly secured between lower and upper sealing plates 243, 244 of compensator housing 220. A locking member 305 may be provided on one, or more, alignment tubes 304 on compensator housing 220, and locking member 305 is selectively engagable with mating openings 306, 307 formed in alignment tube, or tubes, 303 to selectively position compensator housing 220 in at least two locations, or positions, with respect to the linear accelerator 231 as previously described in connection with FIGS. 17–21. FIG. 15 illustrates compensator housing 220 being disposed in the retracted position previously illustrated in FIGS. 19 and 20, and FIG. 16 illustrates compensator housing 220 being disposed in its extended position, as also illustrated in FIGS. 17, 18, and 21.

When using the tissue compensation system 230 and method for making a tissue compensator 301, in accordance with the present invention, data concerning the contoured treatment surface 300 is transferred mechanically and automatically to create tissue compensator 301, and no transcription or manipulation of the data, such as by computer, is necessary. A satisfactory number of rods 238 are able to be used to provide measurements of the contoured treatment surface 300 for each square centimeter of the treatment surface 300. After completion of the radiation therapy upon the portion of patient 233, tissue compensator 301 can be stored, such as in a box, so as to be available for the next time treatment surface 300 of patient 233 is to be treated. Alternatively, compensator housing 230 can be returned to the configuration illustrated in FIG. 7, so that it can be used for making another tissue compensator for another patient.

It is to be understood that the invention is not be limited to the exact details of construction, operation, exact materials or embodiment shown and described, as obvious modifications and equivalents will be apparent to one skilled in the art. For example, a plurality of sliding wall members can be disposed within the compensator housing in lieu of the second membrane, and upon deformation of the first membrane by the elongate rods, the sliding wall members move outwardly within the compensator housing to allow for the tissue equivalent material to conform around the elongate rods. The sliding wall members may then be locked in place so that when a vacuum is applied to the resulting cavity containing the tissue equivalent material, the plurality of beads, or tissue equivalent material, is then frozen in place. Accordingly, the invention is therefore to be limited only by the scope of the appended claims.

I claim:

1. A compensator housing for use with a linear accelerator and a rod framework to provide radiation therapy to a portion of a patient, comprising:
    a first membrane, which is flexible and deformable and has an inner and an outer surface;
    a quantity of material substantially equivalent to tissue of the patient disposed within the first membrane; and
    means for retaining the shape of the first membrane after the first membrane has been deformed by at least some elongate rods associated with the rod framework, whereby the tissue equivalent material is disposed in a spatial relationship within the first membrane to absorb some of the radiation from the radiation therapy upon a radiation beam passing through the first membrane.

2. The compensator housing of claim 1, wherein the shape retaining means includes a first means for creating a vacuum in the compensator housing whereby the first membrane is retained in the deformed shape by the vacuum, and the inner surface of the first membrane bears against the tissue equivalent material.

3. The compensator housing of claim 2, wherein the tissue equivalent material is a plurality of small diameter beads disposed within the first membrane.

4. The compensator housing of claim 3, wherein the beads are formed of polystyrene plastic.

5. The compensator housing of claim 2, wherein the compensator housing includes a second membrane disposed therein, which is flexible and deformable, and has an inner and an outer surface.

6. The compensator housing of claim 5, wherein the compensator housing has an interior surface, and the tissue equivalent material is disposed within a first cavity defined by the inner surfaces of the first and second membranes and at least a first portion of the interior surface of the compensator housing.

7. The compensator housing of claim 6, wherein the first and second membranes are formed integral with each other.

8. The compensator housing of claim 6, wherein the first means for creating a vacuum in the compensator housing is in fluid communication with the first cavity defined by the inner surfaces of the first and second membranes and at least a first portion of the interior surface of the compensator housing.

9. The compensator housing of claim 8, including a second means for creating a vacuum in the compensator housing, the second vacuum creating means being is fluid communication with a second cavity in the compensator housing defined by the outer surface of the second membrane and at least a second portion of the interior surface of the compensator housing.

10. A rod framework for use with a linear accelerator and a compensator housing to provide radiation therapy on a portion of a patient, comprising:
    a plurality of elongate rods, each rod having a longitudinal axis and first and second ends, the first ends adapted to contact a surface on the patient adjacent the portion of the patient to receive the radiation therapy, the rods being mounted for movement in a direction along their longitudinal axes and at least some of the rods being moved, upon the first end of some of the rods contacting the patient;
    at least some of the second ends of the elongate rods being disposed and adapted to contact the compensator housing in response to movement caused by at least some of the first ends of the elongate rods contacting the patient; and
    an upper and a lower plate member, the plate members being spaced apart from each other, and each plate member has a plurality of openings formed therein through which the plurality of rods pass.

11. The rod framework of claim 10, wherein the second ends of the plurality of rods each have an abutment member associated therewith for engagement with the upper plate member to prevent the plurality of rods from completely passing through the openings formed in the upper plate member.

12. The rod framework of claim 10, wherein the upper and lower plate members are disposed in a substantially parallel relationship with each other and a substantial number of the plurality of elongate rods are disposed with their longitudinal axes disposed in a nonperpendicular angular relationship with respect to the upper and lower plate members.

* * * * *